United States Patent [19]
Rosenthal

[11] 3,961,201
[45] June 1, 1976

[54] PATIENT MONITORING
[76] Inventor: Morris H. Rosenthal, 182 Pond St., Sharon, Mass. 02067
[22] Filed: Sept. 6, 1974
[21] Appl. No.: 503,805

[52] U.S. Cl. .............................. 307/116; 200/85 R; 340/272
[51] Int. Cl.² ........................................ H01H 35/00
[58] Field of Search .............. 200/85 R, 85 A, 86 R; 5/317, 345; 340/272, 278, 279, 280; 128/132 R; 116/67 R, 114 R; 307/116

[56] References Cited
UNITED STATES PATENTS
2,818,477  12/1967  Gollhofer ........................ 200/85 R
2,994,889  8/1961   Oblander .......................... 5/345

Primary Examiner—David Smith, Jr.
Attorney, Agent, or Firm—Charles Hieken; Jerry Cohen

[57] ABSTRACT

A tape switch near the edge of a bed frame closes a warning signal circuit when the weight of a patient near the edge of the bed presses on an actuating switch arm that is cantilevered from the bed frame.

10 Claims, 4 Drawing Figures

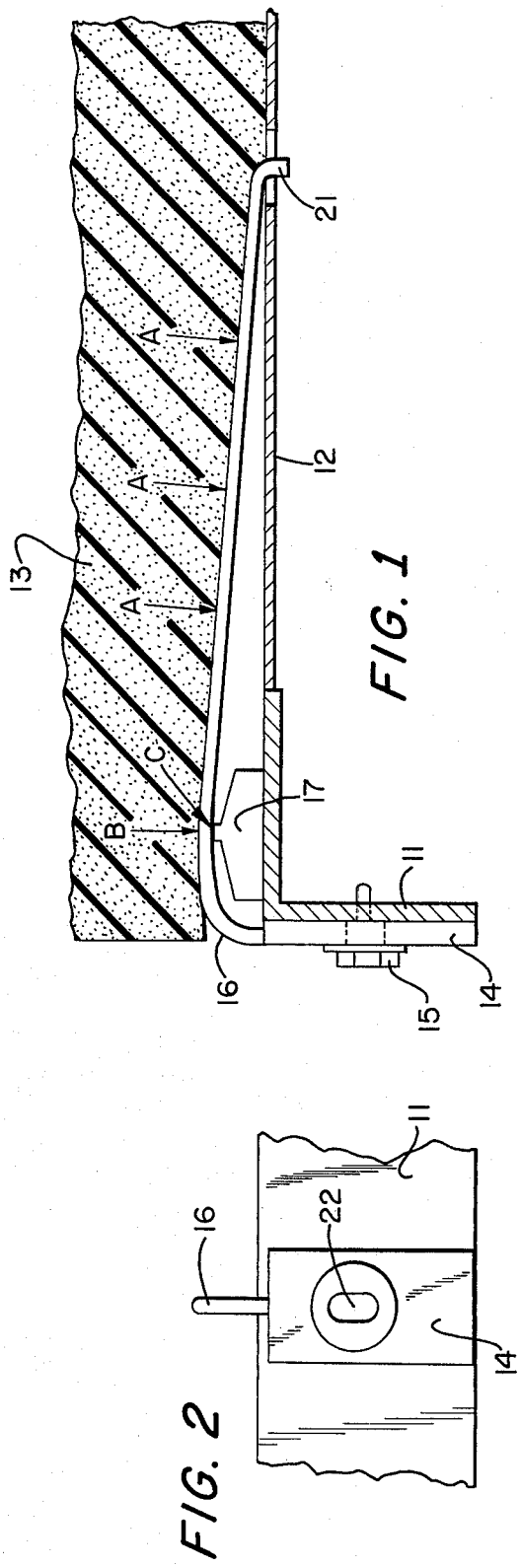
FIG. 1
FIG. 2
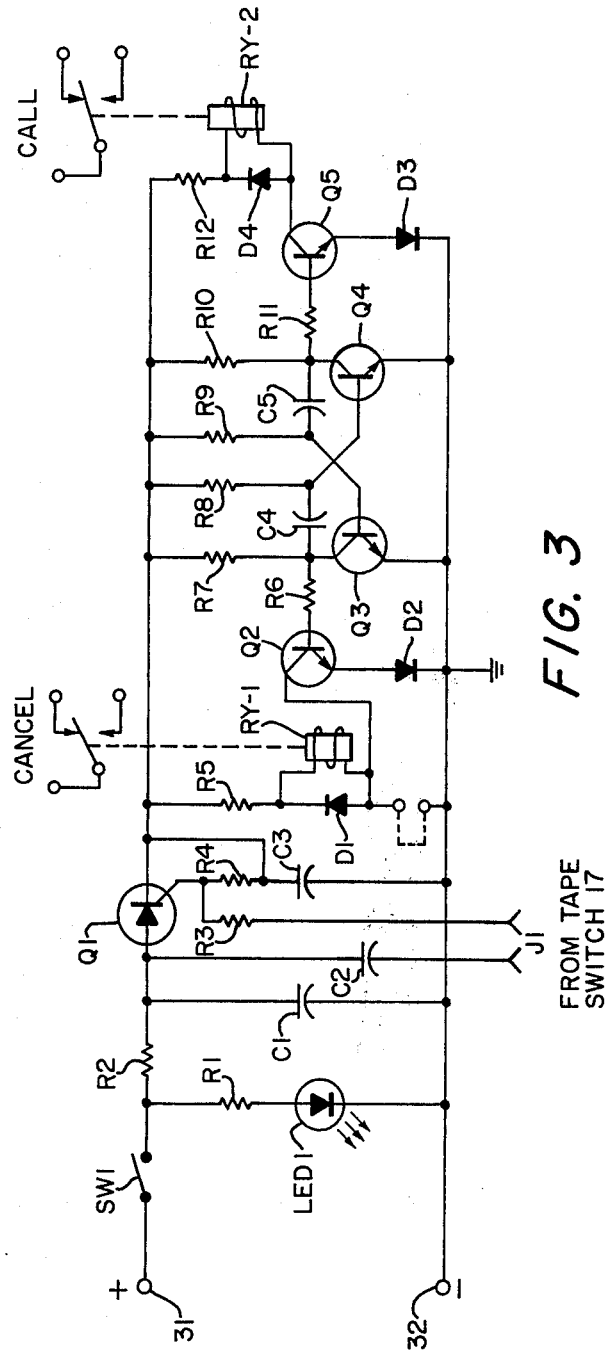
FIG. 3
FIG. 4

PATIENT MONITORING

BACKGROUND OF THE INVENTION

The present invention relates in general to patient monitoring and more particularly concerns novel apparatus and techniques for monitoring a patient and providing a warning when the patient may leave the bed. The invention provides remarkable reliability of monitoring with relatively rugged apparatus relatively free from complexity that may readily be attached to existing hospital beds by relatively unskilled personnel.

A serious problem with bed ridden patients occurs when they leave a bed. Falling out accidentally is one problem. A more common problem occurs when a patient attempting to leave the bed falls. Still another dangerous situation arises when the patient, successful in leaving bed unharmed, falls or trips over an object in the darkened room. These accidents occur because many patients are reluctant to signal for assistance.

Accordingly, it is an important object of the invention to provide methods and means for signalling when a patient is about to leave a bed.

It is a further object of the invention to achieve the preceding object with apparatus that is reliable.

It is a further object of the invention to achieve one or more of the preceding objects with apparatus that is relatively inexpensive and may be attached to existing hospital beds with relatively unskilled personnel.

It is a further object of the invention to achieve one or more of the preceding objects with apparatus suitable for use with existing hospital signalling systems.

It is still a further object of the invention to achieve one or more of the preceding objects with apparatus that is highly resistant to signalling false alarms.

It is a further object of the invention to achieve one or more of the preceding objects with apparatus that is relatively inexpensive to manufacture.

SUMMARY OF THE INVENTION

According to the invention, there are actuable contact means for signalling an alarm condition when actuated located adjacent to the edge of a bed frame. There is switch arm means cantilevered from the edge of the bed frame and extending toward the inside of the bed extending over the actuable contact means beneath the bed mattress for preventing the contact means from being actuated except when the weight of the patient applies enough force to the switch arm means to actuate the contact means as the patient moves toward the edge of the bed.

In a preferred form of the invention actuation of the contact means enables a circuit that provides periodic signalling flashes over the patient call line that continues until a cancel switch is actuated.

Numerous other features, objects and advantages of the invention will become apparent from the following specification when read in connection with the accompanying drawing in which:

BRIEF DESCRIPTION OF THE DRAWING

FIG. 1 is a sectional view through a portion of a hospital bed illustrating a patient monitoring switch according to the invention;

FIG. 2 is a plan view of the switch mounting plate;

FIG. 3 is a schematic circuit diagram of an exemplary embodiment of electronic circuitry for effecting a flashing warning when a patient monitoring switch has been actuated; and FIG. 4 is a diagramatic representation of a bed indicating typical locations where monitoring switches may be placed according to the invention to insure that a patient in position for leaving the bed will actuate the warning system.

DETAILED DESCRIPTION OF PREFERRED EMBODIMENTS

With reference now to the drawing and more particularly FIG. 1 thereof, there is shown a sectional view through a portion of a hospital bed with a patient monitoring switch according to the invention installed helpful in understanding the principles of the invention. The bed frame 11 typically comprises a member of inverted L-shape as shown that typically supports a pan spring 12 (or coil spring assembly) that supports mattress 13. The vertical face of bed spring 11 carries a switch arm mounting plate 14 firmly secured by hex bolt 15 shown seated in a tapped opening in bed frame 11. It may be more convenient to drill a clear opening through the bed frame and use a nut. It may be advantageous to use two fastening means to insure that the switch arm remains in proper alignment. Switch arm mounting plate 14 carries cantilevered switch arm 16 that extends over tape switch 17 secured to the horizontal face of bed frame 11. The free end 21 of switch arm 16 curves downward to reside in a spring opening so that the free end of switch arm 16 normally is positioned between coils of a coil spring or in a hole in a pan spring inside the bed frame. FIG. 2 is a plan view of switch arm mounting plate 14 illustrating the preferred slotted hole 22 to permit vertical alignment of switch arm 16 so that with mattress 13 above it and the patient away from the edge of the bed, switch arm 16 does not actuate tape switch 17, but actuates tape switch 17 when the patient approaches the edge of the bed in the vicinity of the tape switch as described below.

Having briefly described the physical arrangement, the mode of operation will be discussed. The switch assembly of FIG. 1 may be installed in a number of places beneath mattress 13 in areas where the patient would be expected to cross just before leaving bed. The X's in FIG. 4 show typical switch locations. When the patient moves near the area of a switching assembly, the body weight deflects the mattress and switch arm 16 downward, thereby causing the contacts of tape switch 17 to close. Closure of the contacts activates an associated electronic circuit described below which operates the call and cancel function of the nurse call system at approximately 1.5 second intervals, thereby energizing the light above the patient's room and the annunciator and audible warning indicator at the nursing station at the same time intervals. This warning is preferably arranged so that it can be canceled only at the bedside station and without interfering with normal nurse call operations.

A feature of the assembly is that the tape switch contacts will not close under normal body motion of the patient in the bed. When the patient moves toward the switch, his weight causes mattress 13 to compress and deflect switch arm 16 downward at the points A. As the deflection of points A increases, switch arm 16 depresses tape switch 17 at point B until the tape switch contacts close. Deflection of switch arm 16 at points A causes a lever action of switch arm 16 with a deflection at point B less than that at points A. The amount of weight required to effect the switch closure may be changed by adjusting the spacing between switch arm 16 and tape switch 17 at point C. The switching assembly may be used with any type of spring or pan frame.

Referring to FIG. 3, there is shown a schematic circuit diagram of an exemplary embodiment of circuitry for effecting periodic warning signals according to the invention when the tape switch contacts are closed. The circuitry includes SCR Q1 comprising a controlled switch, transistors Q2 and Q5 comprising relay drivers and transistors Q3 and Q4 comprising an astable multivibrator to control the on and off cycle of the warning signal.

Operation of the circuit is as follows. Positive terminal 31 and negative terminal 32 may be connected directly to power from the nurse call system and may operate from supply voltages ranging from 10 to 48 volts D.C. Closing switch SW1 applies power to light emitting diode LED1 functioning as a pilot light and to the anode of SCR Q1.

When the contacts of tape switch 17 close, the gate of SCR Q1 receives a current pulse that passes through resistor R3 and capacitor C2 to turn SCR Q1 on and deliver power to the rest of the circuit.

The astable multivibrator comprising transistors Q3 and Q4 oscillates with a period of approximately 1.5 seconds. The period and ratio of on time to off time may be adjusted by varying the values of capacitors C4 and C5 and resistors R8 and R9. The signals on the collectors of transistors Q3 and Q4 are coupled to the bases of relay drivers Q2 and Q5, respectively. Relays RY1 and RY2 control the cancel and call operations, respectively, of the nurse call system. The relay contacts arrangements permit the circuit to be used with all of the nurse call systems in use today. As the relays operate and release, the call and cancel circuits of the nurse call system are alternately activated, causing the room light to flash, the annunciator at the nursing station to indicate and the bell or buzzer audible alarm to sound approximately every 1.5 seconds. To turn off the alarm, switch SW1 must be opened, removing power from the electronic circuit and automatically canceling the nurse call indication.

In an exemplary embodiment of the invention satisfactorily tested under actual hospital conditions for many weeks, the following circuit parameters were used:

| | | |
|---|---|---|
| R1- 4.7KΩ | C1- 10µf | D1- 1N914 |
| R2- 100Ω | C2- 1µf | D2- 1N914 |
| R3- 10KΩ | C3- 10µf | D3- 1N914 |
| R4- 1KΩ | C4- 22µf | D4- 1N914 |
| R5- 500Ω | C5- 22µf | RY1-Reed Relay 1 Form C |
| R6- 20KΩ | Q1- 2N5061 | RY2-Reed Relay 1 Form C |
| R7- 4.7KΩ | Q2- 2N718 | |
| R8- 180KΩ | Q3- 2N718 | |
| R9- 180KΩ | Q4- 2N718 | |
| R10-4.7KΩ | Q5- 2N718 | |
| R11-20KΩ | | |
| R12-1200Ω | | |

Referring to FIG. 4, there is a plan view of a bed with X's designating typical switch locations. These switches may be connected in parallel across the J1 contacts of the circuit of FIG. 3.

With regard to the broken link in series with the anode of diode D1, some nurse call systems do not require the on-off operation of RY-1, but that RY-1 be energized during the alarm. Putting the jumper in series with anode of D1 will energize RY-1 until the alarm is turned off, and therefore for these call systems, Q2, D2 and R6 can be eliminated from the circuit, and RY-2 provides the call and cancel functions. This, thus permits the use of a single circuit board with various types of call systems.

The particular diodes and transistors were chosen because they are very inexpensive, and operate well over the range of supply voltages encountered in the call systems. Of course there are many similar types which would operate equally as well.

The tapeswitch is manufactured by Tapeswitch Corp. of America, Farmingdale, New York. The particular type used was type 102A, ¾ inch wide × 3/16 inch thick, 40 oz. sensitivity, and mounted to the bed frame using their 106 Coutamould Mounting Channel. The 40 oz. sensitivity was selected as a considered choice, although there is no reason to doubt that the other sensitivities would work also.

There has been described novel apparatus and techniques for reliably monitoring for when a patient is about to leave a bed. The apparatus is relatively easy and inexpensive to fabricate, operates reliably and may be installed by relatively inexperienced personnel. The invention may be used with existing patient call systems. It is evident that those skilled in the art may now make numerous other uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Patient monitoring apparatus comprising,
   actuable contact means located near the edge of a bed frame beneath the mattress for actuation when a patient approaches the edge of the bed,
   and switch arm means for actuating said contact means located between said mattress and said contact means for actuating said contact means when a patient approaches the edge of the bed while preventing said contact means from being actuated when the patient is away from the edge of the bed.

2. Patient monitoring apparatus in accordance with claim 1 wherein said switch arm means is cantilevered from a point at the outside edge of the bed frame with its free end extending inwardly of said outside edge.

3. Patient monitoring apparatus in accordance with claim 2 wherein said switch arm means free end rests above or upon the bed spring.

4. Patient monitoring apparatus in accordance with claim 1 and further comprising,
   electrical circuit means responsive to actuation of said contact means for activating a conventional nurse call system.

5. Patient monitoring apparatus in accordance with claim 1 and further comprising holding plate means secured to a generally vertical face of said bed frame for supporting said switch arm means.

6. Patient monitoring apparatus in accordance with claim 2 wherein said contact means is located between the edge of the bed and said free end.

7. Patient monitoring apparatus in accordance with claim 6 wherein said contact means is closer to the edge of the bed than to said free end.

8. Patient monitoring apparatus in accordance with claim 7 wherein said contact means comprises a tapeswitch.

9. Patient monitoring apparatus in accordance with claim 4 wherein said electrical circuit means includes means defining an astable multivibrator for alternately operating and releasing a relay in response to actuation of said contact means whereby a warning signal in said conventional nurse call system is alternately energized and de-energized by said relay.

10. Patient monitoring apparatus in accordance with claim 9 wherein said electrical circuit means includes SCR means rendered conductive in response to actuation of said contact means in series with a disabling switch for delivering operating power to said astable multivibrator comprising means for continuously flashing said warning signal from the time said contact means is actuated until said disabling switch opens.

\* \* \* \* \*